(12) United States Patent
Kaduk et al.

(10) Patent No.: US 8,697,596 B2
(45) Date of Patent: Apr. 15, 2014

(54) MIXED METAL OXIDE CATALYSTS AND CATALYTIC CONVERSIONS OF LOWER ALKANE HYDROCARBONS

(75) Inventors: James A. Kaduk, Naperville, IL (US); James F. Brazdil, Glen Ellyn, IL (US); Alakananda Bhattacharyya, Glen Ellyn, IL (US); Christos Paparizos, Willoughby, OH (US)

(73) Assignee: INEOS USA LLC, Lisle, IL (US)

( * ) Notice: Subject to any disclaimer, the term of this patent is extended or adjusted under 35 U.S.C. 154(b) by 802 days.

(21) Appl. No.: 11/732,212

(22) Filed: Apr. 3, 2007

(65) Prior Publication Data

US 2008/0249328 A1 Oct. 9, 2008

(51) Int. Cl.
*B01J 23/28* (2006.01)
*B01J 23/22* (2006.01)
*C07C 253/24* (2006.01)
*C07C 53/124* (2006.01)

(52) U.S. Cl.
USPC ........... 502/302; 502/100; 502/304; 502/309; 502/312; 558/321; 562/512.2

(58) Field of Classification Search
USPC .......... 502/100, 302, 304, 309, 312; 558/321; 562/512.2
See application file for complete search history.

(56) References Cited

U.S. PATENT DOCUMENTS

| | | | |
|---|---|---|---|
| 4,760,159 A | 7/1988 | Suresh et al. | |
| 4,797,381 A | 1/1989 | Bartek et al. | |
| 5,011,945 A | 4/1991 | Taheri | |
| 5,049,692 A | 9/1991 | Hatano et al. | |
| 5,231,214 A | 7/1993 | Ushikubo et al. | |
| 5,281,745 A | 1/1994 | Ushikubo et al. | |
| 5,380,933 A | 1/1995 | Ushikubo et al. | |
| 5,422,328 A | 6/1995 | Ushikubo et al. | |
| 5,750,760 A | 5/1998 | Ushikubo et al. | |
| 5,866,502 A | 2/1999 | Cirjak et al. | |
| 6,036,880 A | 3/2000 | Komada et al. | |
| 6,043,185 A | 3/2000 | Cirjak et al. | |
| 6,143,916 A | 11/2000 | Hinago et al. | |
| 6,156,920 A | 12/2000 | Brazdil et al. | |
| 6,407,031 B1 | 6/2002 | Chaturvedi et al. | |
| 6,432,870 B1 | 8/2002 | Tu et al. | |
| 6,514,902 B1 * | 2/2003 | Inoue et al. | 502/305 |
| 6,645,906 B2 | 11/2003 | Bogan et al. | |
| 6,825,380 B2 | 11/2004 | Chaturvedi et al. | |
| 6,867,328 B2 | 3/2005 | Borgmeier et al. | |
| 6,919,295 B2 | 7/2005 | Gaffney et al. | |
| 2003/0088118 A1 | 5/2003 | Komada et al. | |
| 2004/0063990 A1 | 4/2004 | Gaffney et al. | |
| 2004/0092768 A1 | 5/2004 | Borgmeier et al. | |
| 2004/0147393 A1 | 7/2004 | Hibst et al. | |
| 2004/0192966 A1 | 9/2004 | Hazin | |
| 2005/0054869 A1 | 3/2005 | Lugmair et al. | |
| 2006/0122055 A1 | 6/2006 | Gaffney et al. | |
| 2006/0167299 A1 | 7/2006 | Gaffney et al. | |
| 2006/0183942 A1 | 8/2006 | Gaffney et al. | |
| 2008/0194871 A1 | 8/2008 | Dubois et al. | |
| 2008/0248947 A1 * | 10/2008 | Zajac et al. | 502/312 |

FOREIGN PATENT DOCUMENTS

| | | | | |
|---|---|---|---|---|
| EP | 0 123 467 A1 | | 10/1984 | |
| EP | 0 895 809 A1 | | 2/1999 | |
| EP | 1 192 988 | * | 4/2002 | ............... B01J 23/28 |
| EP | 1 346 766 | | 8/2003 | |
| EP | 1 346 766 | * | 9/2003 | ............... B01J 23/28 |
| EP | 1 806 178 A1 | | 7/2007 | |
| GB | 1 464 198 | | 2/1977 | |
| JP | 1-126599 A | | 5/1989 | |
| JP | 50 01714 | | 1/1993 | |
| JP | 1999/114426 A | | 4/1999 | |
| WO | WO 2004 108278 A1 | | 12/2004 | |
| WO | WO 2006 019078 A1 | | 2/2006 | |
| WO | WO 2008 103255 A1 | | 8/2008 | |
| WO | WO 2008 123974 A1 | | 10/2008 | |
| WO | WO 2008 123975 | | 10/2008 | |

* cited by examiner

Primary Examiner — Joseph Kosack

(74) Attorney, Agent, or Firm — David P. Yusko; INEOS USA LLC

(57) ABSTRACT

Catalytic compositions and processes are disclosed for economical conversions of lower alkane hydrocarbons. Broadly, the present invention discloses solid compositions containing mixed metal oxides that exhibit catalytic activity for ammoxidation of lower alkane hydrocarbons to produce an unsaturated nitrile in high yield. Generally, these solid oxide compositions comprise, as component elements, molybdenum (Mo), vanadium (V) niobium (Nb) and at least one active element selected from the group consisting of the elements having the ability to form positive ions. Mixed metal oxide catalytic compositions advantageously comprise one or more crystalline phases at least one of which phases has pre-determined unit cell volume and aspect ratio. Also described are methods for forming the improved catalysts having the desired crystalline structure and ammoxidation processes for conversion of lower alkanes.

12 Claims, No Drawings

MIXED METAL OXIDE CATALYSTS AND CATALYTIC CONVERSIONS OF LOWER ALKANE HYDROCARBONS

TECHNICAL FIELD

The present invention relates to solid compositions containing mixed metal oxides that exhibit catalytic activity for ammoxidation of lower alkane hydrocarbons to produce an unsaturated mononitrile in high yield. The invention particularly relates to catalyst compositions, methods of preparing such catalyst compositions, and methods of using such catalyst compositions. More particularly, solid oxide compositions of the invention comprise, as component elements, molybdenum (Mo), vanadium (V) niobium (Nb) and at least one active element selected from the group consisting of the elements having the ability to form positive ions. Mixed metal oxide compositions of the invention advantageously comprise one or more crystalline phases at least one of which phases has pre-determined unit cell volume and aspect ratio. As will be described in greater detail hereinafter, the present invention provides methods for forming the improved catalysts of the invention and ammoxidation processes for conversion of lower alkanes.

BACKGROUND OF THE INVENTION

Nitriles such as acrylonitrile and methacrylonitrile have long been industrially produced as important intermediates for the preparation of synthetic fibers, synthetic resins, synthetic rubbers and the like. A major use of acrylonitrile is in the form of fibers. Acrylonitrile-butadiene-styrene terpolymers (ABS) are important thermoplastic structural plastics. Nitrile-type rubbers, first commercialized as the German Buna-N type in 1930, are copolymers of acrylonitrile and a diene, usually butadiene.

The currently practiced commercial processes for the production of nitrites, such as acrylonitrile and methacrylonitrile, subject an alkene, i.e., propylene or isobutene, to reaction in a gas phase with ammonia and oxygen in the presence of a catalyst at a high temperature. Generally, the catalyst formulations employed are proprietary to the catalyst supplier, but the technology is well established. Furthermore, it is known to include additional starting materials, including additional reactants, such as molecular oxygen and/or steam, and inert materials, such as nitrogen and carbon dioxide, along with the hydrocarbon starting material.

Recently, in view of the relative abundance of lower alkanes relative to corresponding alkenes, resulting in price differences particularly between propane and propylene or between isobutane and isobutene, attention has been drawn to developing improved catalysts for producing nitrites from these, less expensive, lower alkanes. Propane or isobutane is used as starting material in a so-called ammoxidation reaction with ammonia and oxygen in a gas phase in the presence of a catalyst.

Catalysts containing molybdenum, vanadium, antimony and niobium which have been shown to be effective for conversion of propane to acrylonitrile and isobutane to methacrylonitrile (via an ammoxidation reaction) are described in numerous publications, patents and patent applications. See, for example, U.S. Pat. No. 5,750,760 to Ushikubo et al., U.S. Pat. No. 6,036,880 to Komada et al., U.S. Pat. No. 6,143,916 to Hinago et al., U.S. Pat. No. 6,514,902 to Inoue et al., U.S. Patent Application No. US 2003/0088118 A1 by Komadu et al., U.S. Patent Application No. 2004/0063990 A1 to Gaffney et al., U.S. Patent Application No. 2006/0167299 A1 to Gaffney et al., U.S. Patent Application No. 2006/0122055 A1 to Gaffney et al., U.S. Patent Application No. 2006/0183942 A1 to Gaffney et al., PCT Patent Application No. WO 2004/108278 A1 by Asahi Kasei Kabushiki Kaisha, Japanese Patent Application No. JP 1999/114426 A by Asahi Chemical Co., and Japanese Patent Application No. JP 2000/1126599 A by Asahi Chemical Co.

Oxide catalysts containing molybdenum, tellurium, vanadium and niobium are described in U.S. Pat. No. 5,049,692, U.S. Pat. No. 5,231,214, U.S. Pat. No. 5,281,745, U.S. Pat. No. 5,380,933, and U.S. Pat. No. 5,422,328. Further, oxide catalysts containing molybdenum, vanadium, niobium and antimony are described, for example, U.S. Pat. No. 4,760,159, U.S. Pat. No. 4,797,381, U.S. Pat. Appl. No. 2005/0054869 to Lugmair et al. and U.S. Pat. Appl. No. 2006/0122055 to Gaffney et al. However, none of these methods is fully satisfactory in the yield of the intended nitrites.

Although advancements have been made in the art in connection with catalysts containing molybdenum, vanadium, antimony and niobium effective for conversion of propane to acrylonitrile and isobutane to methacrylonitrile (via an ammoxidation reaction), the catalysts need further improvement before becoming commercially viable. In general, the art-known catalytic systems for such reactions suffer from generally low yields of the desired product.

Due to their extensive industrial uses, there is a continuing need for compositions having better catalytic activity and/or selectivity for ammoxidation of lower alkane hydrocarbons to produce an unsaturated nitrile in high yield It is an object of the invention to overcome one or more of the problems described above.

Other advantages of the invention will be apparent to those skilled in the art from a review of the following detailed description, taken in conjunction with the appended claims.

SUMMARY OF THE INVENTION

In broad aspect, the present invention relates to improved catalyst compositions that exhibit an ability to facilitate ammoxidation of a saturated hydrocarbon to the corresponding unsaturated nitrile in high yield, and processes using these improved catalysts for economical conversions of lower alkane hydrocarbons. In particular, the present invention is directed to an improved catalyst and process for the ammoxidation of propane and/or isobutane to acrylonitrile and/or methacrylonitrile, respectively.

Generally, the solid oxide compositions of the invention comprise, as component elements, molybdenum (Mo), vanadium (V) and at least one active element selected from the group consisting of the elements having the ability to form positive ions, for example antimony (Sb) niobium (Nb), titanium (Ti), and cerium (Ce). In some cases, compositions of the invention, comprise oxides of molybdenum, vanadium, antimony, niobium, at least one element selected from the group consisting of lithium, titanium, tin, germanium, zirconium, hafnium, and optionally at least one lanthanide selected from the group consisting of lanthanum, praseodymium, neodymium, samarium, europium, gadolinium, dysprosium, holmium, erbium, thulium, ytterbium and lutetium.

Mixed metal oxide catalytic compositions advantageously comprise one or more crystalline phases at least one of which phases has pre-determined unit cell volume and aspect ratio. Also described are methods for forming the improved catalysts having the desired crystalline structure and ammoxidation processes for conversion of lower alkanes.

One aspect of the invention is directed to solid compositions that exhibit catalytic activity for ammoxidation of alkane hydrocarbons in the gaseous phase, which comprises one or more crystalline phases at least one of which is a first phase that has a unit cell volume in a range upward from about 2250 Å³ to about 2350 Å³, a first dimension and transverse thereto a second dimension with the proviso that the ratio of first to second dimensions is in a range downward from about 2.5 to about 0.7. Advantageously the first phase that has a unit cell volume in a range upward from about 2255 Å³ to about 2290 Å³. Beneficially the ratio of first to second dimensions is in a range downward from about 1.5 to about 1.0.

More particularly the first phase is a mixed metal oxide comprising molybdenum (Mo), vanadium (V) and at least one other element having the ability to form positive ions and to enhance the catalytic activity of the composition for the ammoxidation of propane and/or isobutane in the gaseous phase. Generally, the first phase is characterized as having the M1 crystalline structure.

In another aspect of the invention the composition that exhibits catalytic activity for ammoxidation of propane in the gaseous phase comprises a mixed metal oxide in particulate form having, as component elements, molybdenum (Mo), vanadium (V), at least one element selected from the group consisting of antimony (Sb) and tellurium (Te), and niobium (Nb), and the first phase is characterized as having the M1 crystalline structure. In yet another aspect the first phase is a mixed metal oxide comprising molybdenum (Mo), vanadium (V), antimony (Sb) and niobium (Nb).

In a particularly useful aspect of the invention at least a portion of the composition is formed under conditions of crystallization by combining sources of metal ions in amounts consistent with a nominal mixed oxide material represented by the empirical formula:

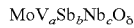

$$MoV_aSb_bNb_cO_\delta$$

where $0.1<a<1.0$, $0.01<b<1.0$, $0.001<c<0.25$, and $\delta$ is the number of oxygen atoms required to maintain electro-neutrality of the other component elements present. At least a portion of the crystalline material is formed by a process which comprises combining the sources of metal ions in aqueous solutions, drying the resulting combined mixture to recover solid materials, and maintaining the recovered solids at elevated temperatures for times sufficient to form at least the first crystalline phase.

In another particularly useful aspect of the invention, at least a portion of the composition is formed under conditions of crystallization by combining sources of metal ions in amounts consistent with a nominal mixed oxide material represented by the empirical formula:

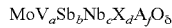

$$MoV_aSb_bNb_cX_dA_fO_\delta$$

where X is selected from the group consisting of Ti, Sn, Ge, Zr, Hf, and mixtures thereof, A is selected from the group consisting of Ce, Nd and mixtures thereof, $0.1<a<1.0$, $0.01<b<1.0$, $0.001<c<0.25$, $0.005<d<0.4$, $0\leq f<0.1$, and $\delta$ is the number of oxygen atoms required to maintain electro-neutrality of the other component elements present with the proviso that one or more of the other elements in the mixed oxide can be present in an oxidation state lower than its highest oxidation state.

At least a portion of the crystalline materials, advantageously according to the invention, are formed by a process which comprises combining the sources of metal ions in aqueous solutions, drying the resulting aqueous mixture to recover solid materials, and maintaining the recovered solids at elevated temperatures for times sufficient to form at least the first crystalline phase.

Beneficially, the aqueous mixtures are reacted at temperatures below about 100° C. and ambient, or near ambient, pressure, and the recovered solid materials are first maintained at elevated temperatures of no more than about 400° C., (typically in a range from about 250° C. to 400° C.), and thereafter in a range upward from about 550° C. to 700° C. and ambient, or near ambient, pressure.

In some cases, the compositions of the invention that exhibit catalytic activity for ammoxidation of propane in the gaseous phase comprises a mixed metal oxide in particulate form having, as component elements, molybdenum (Mo), vanadium (V), antimony (Sb) titanium (Ti), and niobium (Nb). In particularly useful cases the compositions of the invention that exhibit catalytic activity for ammoxidation of propane in the gaseous phase comprises a mixed metal oxide in particulate form having, as component elements, molybdenum (Mo), vanadium (V), antimony (Sb) niobium (Nb), titanium (Ti), and cerium (Ce).

A further aspect of the invention is a process for producing an unsaturated nitrile by catalytic conversion in the gaseous phase of a lower alkane hydrocarbon with ammonia and a source of dioxygen in the presence of a particulate solid which comprises one or more crystalline phases at least one of which is a first phase that has a unit cell volume in a range upward from about 2250 Å³ to about 2350 Å³, a first dimension and transverse thereto a second dimension with the proviso that the ratio of first to second dimensions is in a range downward from about 2.5 to about 0.7.

For a more complete understanding of the present invention, reference should now be made to the embodiments described in greater detail below and by way of examples of the invention.

GENERAL DESCRIPTION

The catalyst of the present invention may be used either supported or unsupported (i.e. the catalyst may comprise a support). Suitable supports are silica, alumina, zirconia, titania, or mixtures thereof. However, when zirconia or titania are used as support materials then the ratio of molybdenum to zirconium or titanium increases over the values shown in the above formulas, such that the Mo to Zr or Ti ratio is between about 1 to 10. A support typically serves as a binder for the catalyst resulting in a harder and more attrition resistant catalyst. However, for commercial applications, an appropriate blend of both the active phase (i.e. the complex of catalytic oxides described above) and the support is helpful to obtain an acceptable activity and hardness (attrition resistance) for the catalyst. Directionally, any increase in the active phase decreases the hardness of the catalyst. The support comprises between 10 and 90 weight percent of the supported catalyst. Typically, the support comprises between 40 and 60 weight percent of the supported catalyst. In one embodiment of this invention, the support may comprise as little as about 10 weight percent of the supported catalyst. In one embodiment of this invention, the support may comprise as little as about 30 weight percent of the supported catalyst. In another embodiment of this invention, the support may comprise as much as about 70 weight percent of the supported catalyst. Support materials are available which may contain one or more promoter elements, and such promoter elements may be incorporated into the catalyst via the support material The catalyst compositions described herein can be prepared by the hydrothermal synthesis methods described herein. Hydrothermal synthesis methods are disclosed in U.S. Patent Application No. 2003/0004379 to Gaffney et al., Watanabe et al., "New Synthesis Route for Mo—V—Nb—Te mixed oxides catalyst for propane ammoxidation", Applied Catalysis A: General, 194-195, pp. 479-485 (2000), and Ueda et al., "Selective Oxidation of Light Alkanes over hydrothermally synthesized Mo—V-M-O (M=Al, Ga, Bi, Sb and Te) oxide catalysts.", Applied Catalysis A: General, 200, pp. 135-145, which are incorporated here by reference.

In general, the catalyst compositions described herein can be prepared by hydrothermal synthesis where precursors for a mixed metal oxide catalyst composition are admixed in an aqueous solution to form a reaction medium and reacting the reaction medium at elevated pressure and elevated temperature in a sealed reaction vessel for a time sufficient to form the mixed metal oxide. In one embodiment, the hydrothermal synthesis continues for a time sufficient to fully react any organic compounds present in the reaction medium, for example, solvents used in the preparation of the catalyst or any organic compounds added with any of the precursor compounds supplying the mixed metal oxide components of the catalyst composition.

The components are reacted in the sealed reaction vessel at a temperature greater than 100° C. and at a pressure greater than ambient pressure to form a mixed metal oxide precursor. In one embodiment, the components are reacted in the sealed reaction vessel at a temperature of at least about 125° C., in another embodiment at a temperature of at least about 150° C., and in yet another embodiment at a temperature of at least about 175° C. In one embodiment, the components are reacted in the sealed reaction vessel at a pressure of at least about 25 psig, and in another embodiment at a pressure of at least about 50 psig, and in yet another embodiment at a pressure of at least about 100 psig. Such sealed reaction vessels may be equipped with a pressure control device to avoid over pressurizing the vessel and/or to regulate the reaction pressure.

In any case, the components are preferably reacted by a protocol that comprises mixing the components during the reaction step. The particular mixing mechanism is not critical, and can include for example, mixing (e.g., stirring or agitating) the components during the reaction by any effective method. Such methods including, for example, agitating the contents of the reaction vessel, for example by shaking, tumbling or oscillating the component-containing reaction vessel. Such methods also include, for example, stirring by using a stirring member located at least partially within the reaction vessel and a driving force coupled to the stirring member or to the reaction vessel to provide relative motion between the stirring member and the reaction vessel. The stirring member can be a shaft-driven and/or shaft-supported stirring member. The driving force can be directly coupled to the stirring member or can be indirectly coupled to the stirring member (e.g., via magnetic coupling). The mixing is generally preferably sufficient to mix the components to allow for efficient reaction between components of the reaction medium to form a more homogeneous reaction medium (e.g., and resulting in a more homogeneous mixed metal oxide precursor) as compared to an unmixed reaction. This results in more efficient consumption of starting materials and in a more uniform mixed metal oxide product. Mixing the reaction medium during the reaction step also causes the mixed metal oxide product to form in the aqueous reaction mixture rather than on the sides of the reaction vessel. This allows more ready recovery and separation of the mixed metal oxide product by techniques such as centrifugation, decantation, or filtration and avoids the need to recover the majority of product from the sides of the reactor vessel. More advantageously, having the mixed metal oxide form in solution allows for particle growth on all faces of the particle rather than the limited exposed faces when the growth occurs out from the reactor wall.

It is generally desirable to maintain some headspace in the reactor vessel. The amount of headspace may depend on the vessel design or the type of agitation used if the reaction mixture is stirred. Overhead stirred reaction vessels, for example, may take 50% headspace. The headspace is filled with ambient air which provides some amount of oxygen to the reaction. However, the headspace, as is known the art, may be filled with other gases to provide reactants like $O_2$ or even an inert atmosphere such as Ar or $N_2$, the amount of headspace and gas within it depends upon the desired reaction as is known in the art.

The components can be reacted in the sealed reaction vessel at an initial pH of not more than about 4. Over the course of the hydrothermal synthesis, the pH of the reaction mixture may change such that the final pH of the reaction mixture may be higher or lower than the initial pH. Preferably, the components are reacted in the sealed reaction vessel at a pH of not more than about 3.5. In some embodiments, the components can be reacted in the sealed reaction vessel at a pH of not more than about 3.0, of not more than about 2.5, of not more than about 2.0, of not more than about 1.5 or of not more than about 1.0, of not more than about 0.5 or of not more than about 0. Preferred pH ranges include a pH ranging from about negative 0.5 to about 4, preferably from about 0 to about 4, more preferably from about 0.5 to about 3.5. In some embodiments, the pH can range from about 0.7 to about 3.3, or from about 1 to about 3. The pH may be adjusted by adding acid or base to the reaction mixture.

The components can be reacted in the sealed reaction vessels at the aforementioned reaction conditions (including for example, reaction temperatures, reaction pressures, pH, stirring, etc., as described above) for a period of time sufficient to form the mixed metal oxide, preferably where the mixed metal oxide comprises a solid state solution comprising the required elements as discussed above, and at least a portion thereof preferably having the requisite crystalline structure for active and selective propane or isobutane oxidation and/or ammoxidation catalysts, as described below. The exact period of time is not narrowly critical, and can include for example at least about three hours, at least about twelve hours, at least about eighteen hours, at least about twenty-four hours, at least about thirty hours, at least about thirty-six hours, at least about forty-two hours, at least about forty-eight hours, at least about fifty-four hours, at least about sixty hours, at least about sixty-six hours or at least about seventy-two hours. Reaction periods of time can be even more than three days, including for example at least about four days, at least about five days, at least about six days, at least about seven days, at least about two weeks or at least about three weeks or at least about one month.

Following the reaction step, further steps of the preferred catalyst preparation methods can include work-up steps, including for example cooling the reaction medium comprising the mixed metal oxide (e.g., to about ambient temperature), separating the solid particulates comprising the mixed metal oxide from the liquid (e.g., by centrifuging and/or decanting the supernatant, or alternatively, by filtering), washing the separated solid particulates (e.g., using distilled water or deionized water), repeating the separating step and washing steps one or more times, and effecting a final separating step.

After the work-up steps, the washed and separated mixed metal oxide can be dried. Drying the mixed metal oxide can be effected under ambient conditions (e.g., at a temperature of about 25° C. at atmospheric pressure), and/or in an oven, for example, at a temperature ranging from about 40° C. to about 150° C., and preferably of about 120° C. over a drying period of about time ranging from about five to about fifteen hours, and preferably of about twelve hours. Drying can be effected under a controlled or uncontrolled atmosphere, and the drying atmosphere can be an inert gas, an oxidative gas, a reducing gas or air, and is typically and preferably air.

As a further preparation step, the dried mixed metal oxide can be treated to form the mixed metal oxide catalyst. Such treatments can include for example calcinations (e.g., including heat treatments under oxidizing or reducing conditions) effected under various treatment atmospheres. The work-up mixed metal oxide can be crushed or ground prior to such treatment, and/or intermittently during such pretreatment. Preferably, for example, the dried mixed metal oxide can be optionally crushed, and then calcined to form the mixed metal oxide catalyst. The calcination is preferably effected in an inert atmosphere such as nitrogen. Preferred calcination conditions include temperatures ranging from about 400° C. to about 700° C., more preferably from about 500° C. to about 650° C., and in some embodiments, the calcination can be at about 600° C.

The treated (e.g., calcined) mixed metal oxide can be further mechanically treated, including for example by grinding, sieving and pressing the mixed metal oxide. Preferably, the catalyst is sieved to form particles having a particle size distribution with a mean particle size ranging from about 100 µm to about 400 µm, preferably from about 120 µm to about 380 µm, and preferably from about 140 µm to about 360 µm.

Some precursor compounds containing and providing the metal components used in the synthesis of the catalyst can be provided to the reaction vessel as aqueous solutions of the metal salts. Some precursor compounds of the metal components can be provided to the reaction vessels as solids or as slurries comprising solid particulates dispersed in an aqueous media. Some precursor compounds of the metal components can be provided to the reaction vessels as solids or as slurries comprising solid particulates dispersed in an non-aqueous solvents or other non-aqueous media.

Suitable precursor compounds for synthesis of the catalysts as described herein include the following. Suitable molybdenum sources include molybdenum(VI) oxide ($MoO_3$), ammonium heptamolybdate and molybdic acid. Suitable vanadium sources include vanadyl sulfate, ammonium metavanadate and vanadium(V) oxide. Suitable antimony sources include antimony(III) oxide, antimony(III) acetate, antimony(III) oxalate, antimony(V) oxide, antimony (III) sulfate, and antimony(III) tartrate. Suitable neodymium sources may include neodymium (III) chloride, neodymium (III) oxide or neodymium (III) isopropoxide, and preferred is neodymium (III) acetate hydrate. Suitable niobium sources include niobium oxalate, niobium peroxo oxalate, ammonium niobium oxalate, ammonium niobium peroxo oxalate, niobium oxide, niobium ethoxide and niobic acid.

Suitable titanium sources include rutile and/or anatase titanium dioxide ($TiO_2$), e.g. Degussa P-25, titanium isopropoxide, TiO(oxalate), TiO(acetylacetonate)$_2$, and titanium alkoxide complexes, such as Tyzor 131. Suitable tin source include tin (II) acetate. Suitable germanium source include germanium(IV) oxide. Suitable zirconium sources include zirconyl nitrate and zirconium (IV) oxide. Suitable hafnium sources include hafnium (IV) chloride and hafnium (IV) oxide.

Suitable cerium source include cerium (III) acetate, cerium (III) oxide, cerium (IV) oxide cerium (III) oxalate, cerium (III) chloride, cerium (IV) ammonium nitrate, cerium (III) nitrate, cerium (IV) ammonium sulfate, cerium (III) sulfate, and cerium (IV) sulfate.

The amount of aqueous solvent in the reaction medium may vary due to the solubilities of the precursor compounds combined to form the particular mixed metal oxide. The amount of aqueous solvent should at least be sufficient to yield a slurry of the reactants. It is typical in hydrothermal synthesis of mixed metal oxides to leave an amount of headspace in the reactor vessel.

The invention contemplates continuous processes for recovery and purification of organic values from hot gaseous mixtures which are obtained by catalytic ammoxidation of a light alkane hydrocarbon compounds. More particularly, this invention relates to recovery and refining of valuable nitrogen-containing organic compounds formed by catalytic oxidation of least one feed compound selected from the group consisting of propane and isobutane in the presence of ammonia to produce a gaseous reactor effluent containing the corresponding unsaturated mononitrile.

Propane is preferably converted to acrylonitrile and isobutane to methacrylonitrile, by providing one or more of the aforementioned catalysts in a gas-phase flow reactor, and contacting the catalyst with propane or isobutane in the presence of oxygen (e.g. provided to the reaction zone in a feedstream comprising an oxygen-containing gas, such as and typically air) and ammonia under reaction conditions effective to form acrylonitrile or methacrylonitrile. For this reaction, the feed stream preferably comprises propane or isobutane, an oxygen-containing gas such as air, and ammonia with the following molar ratios of: propane or isobutane to oxygen in a ratio ranging from about 0.125 to about 5, and preferably from about 0.25 to about 2.5, and propane or isobutane to ammonia in a ratio ranging from about 0.3 to about 2.5, and preferably from about 0.5 to about 2.0. The feed stream can also comprise one or more additional feed components, including acrylonitrile or methacrylonitrile product (e.g., from a recycle stream or from an earlier-stage of a multi-stage reactor), and/or steam. For example, the feedstream can comprise about 5 percent to about 30 percent by weight relative to the total amount of the feed stream, or by mole relative to the amount of propane or isobutane in the feed stream. In one embodiment the catalyst compositions described herein are employed in the ammoxidation of propane to acrylonitrile is a once-through process, i.e., it operates without recycle of recovered but unreacted feed materials.

The specific design of the gas-phase flow reactor is not narrowly critical. Hence, the gas-phase flow reactor can be a fixed-bed reactor, a fluidized-bed reactor, or another type of reactor. The reactor can be a single reactor, or can be one reactor in a multi-stage reactor system. Preferably, the reactor comprises one or more feed inlets for feeding a reactant feedstream to a reaction zone of the reactor, a reaction zone comprising the mixed metal oxide catalyst, and an outlet for discharging reaction products and unreacted reactants.

The reaction conditions are controlled to be effective for converting the propane to acrylonitrile, respectively, or the isobutane to methacrylonitrile. Generally, reaction conditions include a temperature ranging from about 300° C. to about 550° C., preferably from about 325° C. to about 500° C., and in some embodiments from about 350° C. to about 450° C., and in other embodiments from about 430° C. to about 520° C. Generally, the flow rate of the propane or isobutene containing feedstream through the reaction zone of the gas-phase flow reactor can be controlled to provide a weight hourly space velocity (WHSV) ranging from about 0.02 to about 5, preferably from about 0.05 to about 1, and in some embodiments from about 0.1 to about 0.5, in each case, for example, in grams propane or isobutane to grams of catalyst. The pressure of the reaction zone can be controlled to range from about 0 psig to about 200 psig, preferably from about 0 psig to about 100 psig, and in some embodiments from about 0 psig to about 50 psig.

The resulting acrylonitrile or methacrylonitrile product can be isolated, if desired, from other side-products and/or from unreacted reactants according to methods known in the art.

The catalyst compositions described herein when employed in the single pass (i.e. no recycle) ammoxidation of propane are capable of producing a yield of about 57-58 percent acrylonitrile, with a selectivity of about 24% to $CO_x$ (carbon dioxide+carbon monoxide), and a selectivity of about 13% to a mixture of hydrogen cyanide (HCN) and acetonitrile or methyl cyanide ($CH_3CN$). The effluent of the reactor may also include unreacted oxygen ($O_2$), ammonia ($NH_3$) and entrained catalyst fines.

Processes for recovery and purification of the reaction products include quenching the gaseous reactor effluent with an aqueous quench liquid; forming an aqueous solution comprising the corresponding unsaturated mononitrile, hydrogen cyanide and other organic co-products; and using an integrated sequence of distillations and phase separations to recover for recycle of a useful aqueous liquid, and obtain valuable nitrogen-containing organic compounds and hydrogen cyanide products.

Propane, ammonia and oxygen mix together in the reactor and oxidation of propylene in the presence of ammonia takes place on the surface of the fluidized catalyst. A set of complex exothermic reactions takes place, thereby forming the following products: acrylonitrile, hydrogen cyanide, carbon dioxide, carbon monoxide, acetonitrile, acrolein, acrylic acid, water, other higher nitrites, aldehydes, ketones, acetic acid and a number of miscellaneous unknown organic compounds. Conversions of the three feeds generally are less than 100 percent, thus unreacted propane, ammonia, oxygen and/or nitrogen may be contained in the reactor effluent gas. The source of propane typically contains a small amount of propylene and some heavier hydrocarbon compounds most of which are purged from the process unreacted. A portion of the heat of the exothermic reaction is removed by sets of steam coils which generate and superheat waste steam at approximately 600 psig for process uses such as heat input for distillations in the products recovery and purification section of the process. Reactor effluent gas passes through cyclones, which remove catalyst fines from the gas. The gas is then further cooled in a reactor effluent cooler, which is comprised of a shell and tube exchanger using boiler feed-water as the cooling source.

As is well known, performance of the oxidation catalysts is an important factor, perhaps the most significant factor, in the economics of this and other oxidation processes. Catalyst performance is measured by activity, i.e., conversion of reactants, selectivity, i.e. conversion of reactant to desired product, rate of production of desired product per unit of reactor volume per unit of time, and catalyst life, i.e. effective time on-stream before significant loss of activity or selectivity.

Factors upon which catalyst performance depends include composition, the methods of preparation, support, and calcination conditions. In addition to chemical performance requirements, other key properties include surface area, porosity, density, pore size distribution, hardness, strength, and resistance to mechanical attrition, particularly for fluid bed catalysts.

Typically, the ammoxidation process is carried out in a fluid-bed reactor. Where high alkane conversions are obtained, a single pass system is satisfactory with a residence time of a few seconds is typical. Commercially recoverable quantities of acetonitrile and hydrocyanic acid are optional co-products. Approximately stoichometric quantities of propane, ammonia, and dioxygen are introduced into a fluidized bed of catalytic particles. Suitable operating conditions include pressures in a range from about 3 to about 35 psig (20.7 to 241.4 kPa gage), more preferably from about 5 to about 25 psig (34.5 to 172.4 kPa gage). Generally, temperatures are in a range from about 700° to 1000° F. (371° to 538° C.), preferable in a range from about 750° to 950° F. (399° to 510° C.). Heat of reaction is removed by generation of steam to control the temperature and generating steam at temperatures of from about 300° to about 500° C. elevated pressure.

EXAMPLES OF THE INVENTION

The following examples will serve to illustrate certain specific embodiments of the inventions herein disclosed. These Examples should not, however, be construed as limiting the scope of the novel invention as there are many variations which may be made thereon without departing from the spirit of the disclosed invention, as those of skill in the art will recognize.

General

In order to illustrate the instant invention, samples of a base catalyst, with and without various catalyst modifiers, were prepared and then evaluated under similar reaction conditions. The compositions listed below are nominal compositions, based on the total metals added in the catalyst preparation. Since some metals may be lost or may not completely react during the catalyst preparation, the actual composition of the finished catalyst may vary slightly from the nominal compositions shown below. Description of Phase Analysis of M1-containing Mixed Oxide Catalysts The phase composition of mixed metal oxide catalysts were quantified by applying the Rietveld method (See R. A. Young, *The Rietveld Method. IUCr Monographs on Crystallography* 5. Oxford University Press (1993).) to X-ray powder diffraction data using GSAS (See A. C. Larson and R. B. Von Dreele, *General Structure Analysis System (GSAS)*, Los Alamos National Laboratory Report LAUR 86-748 (2004).) or equivalent software. The structural model of M1 published in P. DeSanto Jr., D. J. Buttrey, R. K. Grasselli, C. G. Lugmair, A. F. Volpe Jr., B. H. Toby, and T. Vogt, *Z. Krist.*, 219, 152-165 (2004), was used in the Retveld refinements.

The M1 lattice parameters were refined (as well as a specimen displacement coefficient), and the unit cell volume was calculated from them. The M1 peak profiles were described using an anisotropic size broadening model (X and ptec profile coefficients, with [001] (Pba2) as the unique axis). The average crystallite size parallel and perpendicular to [001] were calculated from the refined profile coefficients using the equations given in the "Interpretation of Constant Wavelength Profile Coefficients" section of the GSAS manual. The aspect ratio was calculated by (size(parallel)/size(perpendicular)).

Description of Catalyst Preparation:

Ammonium heptamolybdate, ammonium metavanadate and diantimony trioxide are added to water, followed by heating of the resultant mixture to temperatures of at least 50° C. and thereby obtain an aqueous mixture (A). It is preferred that the heating is performed while stirring the mixture. Advantageously the aqueous mixture is heated to temperatures in the range upward from 70° C. to the normal boiling point of the mixture. The heating may be performed under reflux by using equipment having a reflux condenser. In the case of heating under reflux, the boiling point generally is in the range of from about 101° C. to 102° C. Elevated temperatures are maintained for 0.5 hour or more. When the heating temperature is low (e.g., lower than 50° C.), the heating time needs to be long. When the heating temperature is in a range of from 80° C. to 100° C., the heating time is typically in a range of from 1 to 5 hours.

Beneficially, after the heating, silica sol and hydrogen peroxide are added to the aqueous mixture (A). When hydrogen peroxide is added to the aqueous mixture (A), the amount of the hydrogen peroxide is such that the molar ratio of hydrogen peroxide to antimony ($H_2O_2$/Sb molar ratio) compound in terms of antimony is in the range of from 0.01 to 20, advantageously in the range of from 0.5 to 3, more advantageously in the range of from 1 to 2.5. After addition of hydrogen peroxide, aqueous mixture (A) is stirred at temperatures in the range of from 30° C. to 70° C. for from 30 minutes to 2 hours.

An aqueous liquid (B) is obtained by adding a niobium compound (e.g., niobic acid) to water, followed by heating of the resultant mixture to temperatures in a range of from 50° C. up to nearly 100° C. Advantageously aqueous liquid (B) contains a dicarboxylic acid (e.g., oxalic acid) in addition to the niobium compound. Generally, the molar ratio of the dicarboxylic acid to the niobium compound in terms of niobium is in the range of from 1 to 4, advantageously in the range of from 2 to 4. That is, in this case, niobic acid and oxalic acid are added to water, followed by heating and stirring of the resultant mixture to thereby obtain an aqueous liquid (B).

A useful method for preparing the above-mentioned aqueous liquid (B), comprises the following steps: (1) mixing water, a dicarboxylic acid (e.g. oxalic acid) and a niobium compound (e.g. niobic acid) thereby obtaining a preliminary niobium-containing aqueous solution or a niobium-containing aqueous mixture having suspended therein a part of the niobium compound; (2) cooling the preliminary niobium-containing aqueous solution or niobium-containing aqueous mixture thereby precipitating a part of the dicarboxylic acid; and (3) removing the precipitated dicarboxylic acid from the preliminary niobium-containing aqueous solution, or removing the precipitated dicarboxylic acid and the suspended niobium compound from the niobium-containing aqueous mixture, thereby obtaining a niobium-containing aqueous liquid (B). Aqueous liquids (B) obtained in the above method usually have a dicarboxylic acid/niobium molar ratio within the range of from 2 to 4.

A particularly useful dicarboxylic acid is oxalic acid, and useful niobium compounds in step (1) of this method include niobic acid, niobium hydrogenoxalate and ammonium niobium oxalate. These niobium compounds can be used in the form of a solid, a mixture, or a dispersion in an appropriate medium. When either niobium hydrogenoxalate or ammonium oxalate is used as the niobium compound, the dicarboxylic acid may not be used. When niobic acid is used as the niobium compound, in order to remove acidic impurities with which the niobic acid may have been contaminated during the production thereof, the niobic acid may be washed with an aqueous ammonia solution and/or water prior to use. It is preferred to use, as the niobium compound, a freshly prepared niobium compound. However, in the above-mentioned method, a niobium compound can be used which is slightly denatured (for example by dehydration) as a result of a long-term storage and the like. In step (1) of this method, the dissolution of the niobium compound can be promoted by the addition of a small amount of aqueous ammonia or by heating.

The concentration of the niobium compound (in terms of niobium) in the preliminary niobium-containing aqueous solution or aqueous mixture is preferably maintained within the range of from 0.2 to 0.8 mol/kg of the solution or mixture. The dicarboxylic acid is preferably used in an amount such that the molar ratio of dicarboxylic acid to niobium compound in terms of niobium is approximately 3 to 6. When an excess amount of the dicarboxylic acid is used, a large amount of the niobium compound can be dissolved in the aqueous solution of dicarboxylic acid; however, a disadvantage is likely to arise in that the amount of the dicarboxylic acid which is caused to precipitate by cooling the obtained preliminary niobium-containing aqueous solution or mixture becomes too large, thus decreasing the utilization of the dicarboxylic acid. On the other hand, when an unsatisfactory amount of the dicarboxylic acid is used, a disadvantage is likely to arise in that a large amount of the niobium compound remains undissolved and is suspended in the aqueous solution of the dicarboxylic acid to form a mixture, wherein the suspended niobium compound is removed from the aqueous mixture, thus decreasing the degree of utilization of the niobium compound.

Any suitable method of cooling may be used in step (2). For example, the cooling can be performed simply by means of an ice bath.

The removal of the precipitated dicarboxylic acid (or precipitated dicarboxylic acid and the dispersed niobium compound) in step (3) can be easily performed by conventional methods, for example, by decantation or filtration.

When the dicarboxylic acid/niobium molar ratio of the obtained niobium-containing aqueous solution is outside the range of from 2 to 4, either the niobium compound or dicarboxylic acid may be added to the aqueous liquid (B) so that the dicarboxylic acid/niobium molar ratio of the solution falls within the above-mentioned range. However, in general, such an operation is unnecessary since an aqueous liquid (B) having the dicarboxylic acid/niobium molar ratio within the range of from 2 to 4 can be prepared by appropriately controlling the concentration of the niobium compound, the ratio of the dicarboxylic acid to the niobium compound and the cooling temperature of the above-mentioned preliminary niobium-containing aqueous solution or aqueous mixture.

The aqueous liquid (B) may also be prepared comprising further component(s). For example, at least a part of the aqueous liquid (B) containing a niobium compound or containing a mixture of a niobium compound and a dicarboxylic acid is used together with hydrogen peroxide. In this case, it is beneficial that the amount of hydrogen peroxide provided a molar ratio of hydrogen peroxide to niobium compound ($H_2O_2$/Nb molar ratio) in terms of niobium is in the range of from 0.5 to 20, preferably in the range of from 1 to 20.

In another example, at least part of the aqueous liquid (B), containing a niobium compound or containing a mixture of a niobium compound and a dicarboxylic acid, or a mixture thereof with hydrogen peroxide, further comprises an antimony compound (e.g. diantimony trioxide), a titanium compound (e.g. titanium dioxide, which can be a mixture of rutile and anatase forms) and/or a cerium compound (e.g. cerium acetate). In this case, the amount of the hydrogen peroxide is such that the molar ratio of hydrogen peroxide to niobium compound ($H_2O_2$/Nb molar ratio) in terms of niobium is in the range of from 0.5 to 20, preferably in the range of from 1 to 20. In another example, the antimony compound mixed with the at least a part of the aqueous liquid (B) and the hydrogen peroxide is such that the molar ratio (Sb/Nb molar ratio) of the antimony compound in terms of antimony to the niobium compound in terms of niobium is not more than 5, preferably in the range of from 0.01 to 2.

Aqueous mixture (A) and aqueous liquid (B) are mixed together in an appropriate ratio in accordance with the desired composition of the catalyst, to thereby providing an aqueous mixture of ingredients, typically, in the form of a slurry. The content of ingredients in the aqueous mixture is generally in a range upward from about 50 percent by weight, preferably in the range of from 70 to 95 percent by weight, more preferably in the range of from 75 to 90 percent by weight.

In the case of producing a silica carrier-supported catalyst of the present invention, the aqueous raw material mixture is prepared so as to contain a source of silica (namely, a silica sol or fumed silica). The amount of the source of silica can be appropriately adjusted in accordance with the amount of the silica carrier in the catalyst to be obtained.

Drying Step

The aqueous mixture of ingredients is dried to thereby provide a dry catalyst precursor. Drying may be conducted by conventional methods, such as spray drying or evaporation drying. Spray drying is particularly useful, because a fine, spherical, dry catalyst precursor is obtained. The spray drying can be conducted by centrifugation, by the two-phase flow nozzle method or by the high-pressure nozzle method. As a heat source for drying, it is preferred to use air which has been heated by steam, an electric heater and the like. It is preferred that the temperature of the spray dryer at an entrance to the dryer section thereof is from 150° C. to 300° C.

Calcination Step

In the calcination step, the dry catalyst precursor is converted into a mixed metal oxide catalyst. Calcinations can be conducted using a rotary kiln, a fluidized-bed kiln or the like. When calcination of the dry catalyst precursor is conducted in a stationary state, problems possibly arise in that the precursor cannot be evenly calcined, thus leading to a deterioration of the properties of the catalyst obtained and also to a breakage or cracking of the catalyst obtained.

Conditions of calcination preselected such that the catalyst formed has a specific surface are of from 5 m²/g to 30 m²/g. Typically, calcination is conducted under calcination conditions wherein the heating temperature of the dry catalyst precursor is continuously or intermittently elevated from a temperature which is less than 400° C. to a temperature which is in the range of from 550° C. to 700° C. Advantageously, the conditions of calcination are preselected such that the resulting catalyst comprises one or more crystalline phases at least one of which is a first phase that has a unit cell volume in a range upward from about 2200 A³, a first crystallite dimension and a transverse thereto a second dimension with the proviso that the ratio of first to second dimensions is in a range downward from about 2.5. The calcination can be conducted in air or under a flow of air. However, at least a part of the calcination is preferably conducted in an atmosphere of an inert gas (e.g., under a flow of an inert gas), such as nitrogen gas that is substantially free of oxygen.

Catalyst Testing

Catalyst was evaluated in a 40 cc fluid bed reactor having a diameter of 1-inch. The reactor was charged with about 20 to 45 g of particulate catalyst. Propane was fed into the reactor at a rate of about 0.05 to 0.15 WWH (i.e., weight of propane/weight of catalyst/hour). Ammonia was fed into the reactor at a flow rate such that ammonia to propane ratio was in the range for about 1 to 1.5. Pressure inside the reactor was maintained at about 2 to 15 psig. Reaction temperatures were in the range of about 420 to 460° C.

Example 1

This example demonstrates preparation of a mixed metal oxide catalyst having a nominal composition represented by

$MoV_{0.27}Sb_{0.2}Nb_{0.06}Ti_{0.1}Nd_{0.005}O_n$ (Preparation of an Aqueous Mixture of Ingredients)

This method used vanadium pentoxide ($V_2O_5$) and excess oxalic acid ($HO_2CCO_2H$). A solution was prepared by dissolving 331 g of niobic acid ($Nb_2O_5 \cdot nH_2O$) while stirring in a solution prepared by dissolving 751 g oxalic acid in 3750 g water at 60° C. (Solution 1)

A slurry was prepared by mixing 4783 g of molybdenum trioxide ($MoO_3$), 816 g of vanadium pentoxide ($V_2O_5$), 969 g of antimony (III) oxide ($Sb_2O_3$), 265 g $TiO_2$, 56 g of neodymium acetate ($Nd(acetate)_3 \cdot 1.0H_2O$), and 25670 g of water (Mixture 2).

All of mixture 2 was placed into a 20-gal reactor to which solution 1 was added. Additional oxalic acid (420 g) was added into the reactor. During these additions 18675 g of water was used for rinsing purpose. The reactor was heated to 175° C., under nitrogen, and stirred at 400 rpm for two days. After two days the reactor was cooled down to about 40° C. and the resulting hydrothermally prepared slurry (HT Slurry) was emptied to a Teflon-coated pail.

(Preparation of a Dried Catalyst Precursor)

A portion of the HT Slurry was mixed with a silica sol and spray dried to obtain a dried catalyst precursor containing 30 percent silica.

(Calcination to Form a Mixed Oxide Catalyst)

A portion of the dried catalyst precursor was charged into a rotary calciner, and calcined under nitrogen in two steps; initially at 225° C. and thereafter at 600° C.

Example 2

In this example higher temperatures are used in the two step calcination for the preparation of a mixed metal oxide catalyst having a nominal composition represented by

$MoV_{0.27}Sb_{0.2}Nb_{0.06}Ti_{0.1}Nd_{0.005}O_n$ (Preparation of an Aqueous Mixture of Ingredients)

This method used vanadium pentoxide ($V_2O_5$) and excess oxalic acid. A solution was prepared by dissolving 331 g of niobic acid while stirring in a solution prepared by dissolving 751 g oxalic acid in 3750 g water at 60° C. (Solution 1)

A slurry was prepared by mixing 4783 g of molybdenum trioxide ($MoO_3$), 816 g of vanadium pentoxide ($V_2O_5$), 969 g of antimony (III) oxide ($Sb_2O_3$), 265 g $TiO_2$, 56 g of neodymium acetate ($Nd(acetate)_3 \cdot 1.0H_2O$), and 25670 g of water (Mixture 2).

All of mixture 2 was placed into a 20-gal reactor to which solution 1 was added. Additional oxalic acid (420 g) was added into the reactor. During these additions 18675 g of water was used for rinsing purpose. The reactor was heated to 175° C., under nitrogen, and stirred at 400 rpm for two days. After two days the reactor was cooled down to about 40° C. and the resulting hydrothermally prepared slurry (HT Slurry) was emptied to a Teflon-coated pail.

(Preparation of a Dried Catalyst Precursor)

A portion of the HT Slurry was mixed with a silica sol and spray dried to obtain a dried catalyst precursor containing 30 percent silica.

(Calcination to Form a Mixed Oxide Catalyst)

A portion of the dried catalyst precursor was charged into a rotary calciner, and calcined under nitrogen in two steps; initially at 345° C. and thereafter at 620° C.

Example 3

In this example a single higher temperature was used in the calcination for the preparation of a mixed metal oxide catalyst having a nominal composition represented by

$MoV_{0.27}Sb_{0.2}Nb_{0.06}Ti_{0.1}Nd_{0.005}O_n$ (Preparation of an Aqueous Mixture of Ingredients)

This method used vanadium pentoxide ($V_2O_5$) and excess oxalic acid. A solution was prepared by dissolving 331 g of niobic acid while stirring in a solution prepared by dissolving 751 g oxalic acid in 3750 g water at 60 C (Solution 1)

A slurry was prepared by mixing 4783 g of molybdenum trioxide ($MoO_3$), 816 g of vanadium pentoxide ($V_2O_5$), 969 g of antimony (III) oxide ($Sb_2O_3$), 265 g $TiO_2$, 56 g of neodymium acetate ($NdCe(acetate)_3 \cdot 1.0H_2O$), and 25670 g of water (Mixture 2).

All of mixture 2 was placed into a 20-gal reactor to which solution 1 was added. Additional oxalic acid (420 g) was added into the reactor. During these additions 18675 g of water was used for rinsing purpose. The reactor was heated to 175° C., under nitrogen, and stirred at 400 rpm for two days. After two days the reactor was cooled down to about 40° C. and the resulting hydrothermally prepared slurry (HT Slurry) was emptied to a Teflon-coated pail.

(Preparation of a Dried Catalyst Precursor)

A portion of the HT Slurry was mixed with a silica sol and spray dried to obtain a dried catalyst precursor containing 30 percent silica.

(Calcination to Form a Mixed Oxide Catalyst)

A portion of the dried catalyst precursor was charged into a rotary calciner, and calcined under nitrogen at 700° C.

Example 4

This example demonstrates a non-hydrothermal preparation of a mixed metal oxide catalyst having a nominal composition represented by $MoV_{0.3}Sb_{0.2}Nb_{0.08}Ti_{0.1}Ce_{0.005}O_n$ (Preparation of an Aqueous Mixture of Ingredients)

A solution was prepared by mixing 222.4 g ammonium heptamolybdate tetrahydrate and 1160 g water. To this solution was added 44.22 g ammonium metavanadate and 30.67 g $Sb_2O_3$. The mixture was heated to 90 C and stirred for 2.5 hours. The solution was then cooled to 70 C and 466.9 g of a Nalco silica sol (96SN036, 32% solids) and 44.5 g of 30% $H_2O_2$ was added. The solution was stirred for 1 hour at 50 C. (Mixture 1)

Another mixture was prepared by adding 6.1 g of $Sb_2O_3$ to a 153.7 g of a 0.63 molar (in Nb) niobic acid/oxalic acid solution, previously prepared. To this mixture were added 38.5 g of 30% $H_2O_2$, 2.07 g $Ce(acetate)_3 \cdot 1.5H_2O$ and 10.07 g of $TiO_2$. The mixture was stirred for 30 min at room temperature (Mixture 2).

(Preparation of a Dried Catalyst Precursor)

Mixture 2 was added to Mixture 1 while stirring. To this was added a solution prepared by mixing 74.7 g fumed silica and 1125 g water. The final mixture was stirred for 15 min and spray dried.

(Calcination to Form a Mixed Oxide Catalyst)

About 75 g of this spray-dried material was calcined under nitrogen in a 1-foot vertical tube in two steps. After raising the temperature of the loaded vertical tube at the rate of about 1.2° C./min, to 345° C., the temperature was maintained at 345 C for 4 hours. In the $2^{nd}$ step the temperature was again raised at the rate of about 2.3° C./min to a temperature of 600° C. This calcination was completed by maintaining temperature at 600° C. for 2 hours. This catalyst was evaluated in a 40 cc fluid bed reactor.

Example 5

In this example a single higher temperature was used in the calcination for the non-hydrothermal preparation of a mixed metal oxide catalyst having a nominal composition represented by

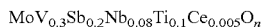
$MoV_{0.3}Sb_{0.2}Nb_{0.08}Ti_{0.1}Ce_{0.005}O_n$ (Preparation of an Aqueous Mixture of Ingredients)

A solution was prepared by mixing 222.4 g ammonium heptamolybdate tetrahydrate and 1160 g water. To this solution was added 44.22 g ammonium metavanadate and 30.67 g $Sb_2O_3$. The mixture was heated to 90 C and stirred for 2.5 hours. The solution was then cooled to 70 C and 466.9 g of a Nalco silica sol (96SN036, 32% solids) and 44.5 g of 30% $H_2O_2$ was added. The solution was stirred for 1 hour at 50° C. (Mixture 1)

Another mixture was prepared by adding 6.1 g of $Sb_2O_3$ to a 153.7 g of a 0.63 molar (in Nb) niobic acid/oxalic acid solution, previously prepared. To this mixture were added 38.5 g of 30% $H_2O_2$, 2.07 g $Ce(acetate)_3 \cdot 1.5H_2O$ and 10.07 g of $TiO_2$. The mixture was stirred for 30 min at room temperature (Mixture 2).

(Preparation of a Dried Catalyst Precursor)

Mixture 2 was added to Mixture 1 while stirring. To this was added a solution prepared by mixing 74.7 g fumed silica and 1125 g water. The final mixture was stirred for 15 min and spray dried.

(Calcination to Form a Mixed Oxide Catalyst)

About 75 g of this spray-dried material was calcined under nitrogen in a 1-foot vertical tube in two steps. After raising the temperature of the loaded vertical tube at the rate of about 1.2° C./min, to 345° C., the temperature was maintained at 345° C. for 4 hours. In the $2^{nd}$ step the temperature was again raised at the rate of about 2.3° C./min to a temperature of 640° C. This calcination was completed by maintaining the temperature at 640° C. for 2 hours. This catalyst was evaluated in a 40 cc fluid bed reactor.

Example 6

In this example higher temperatures are used in the two step calcination for the non-hydrothermal preparation of a mixed metal oxide catalyst having a nominal composition represented by

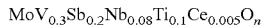
$MoV_{0.3}Sb_{0.2}Nb_{0.08}Ti_{0.1}Ce_{0.005}O_n$ (Preparation of an Aqueous Mixture of Ingredients)

A solution was prepared by mixing 229.4 g ammonium heptamolybdate tetrahydrate and 1160 g water. To this solution was added 45.6 g ammonium metavanadate and 31.7 g $Sb_2O_3$. The mixture was heated to 90° C. and stirred for 2.5 hours. The solution was then cooled to 70° C. and 456.3 g of a Nalco silica sol (96SN036, 32% solids) and 51 g of 30% $H_2O_2$ was added. The solution was stirred for 1 hour at 50° C. (Mixture 1)

Another mixture was prepared by adding 6.26 g of $Sb_2O_3$ to a 123.8 g of a 0.63 molar (in Nb) niobic acid/oxalic acid solution, previously prepared. To this mixture were added 32 g of 30% $H_2O_2$, 2.238 g $Ce(acetate)_3 \cdot 1.5H_2O$ and 10.39 g of $TiO_2$. The mixture was stirred for 30 min at room temperature (Mixture 2).

(Preparation of a Dried Catalyst Precursor)

Mixture 2 was added to Mixture 1 while stirring. To this was added a solution prepared by mixing 73.6 g fumed silica and 1125 g water. The final mixture was stirred for 15 min and spray dried.

(Calcination to Form a Mixed Oxide Catalyst)

About 75 g of this spray-dried material was calcined under nitrogen in a 1-foot vertical tube in two steps. After raising the temperature of the loaded vertical tube at the rate of about 1.2° C./min, to 345° C., the temperature was maintained at 345° C. for 4 hours. In the $2^{nd}$ step the temperature was again raised at the rate of about 2.3° C./min to a temperature of 640° C. This calcination was completed in 2 hours by maintaining the temperature at 640° C. This catalyst was evaluated in a 40 cc fluid bed reactor.

Example 7

This example demonstrates a non-hydrothermal preparation of a mixed metal oxide catalyst having a nominal composition represented by $$MoV_{0.3}Sb_{0.2}Nb_{0.08}Ti_{0.1}Ce_{0.005}O_n$$

(Preparation of an Aqueous Mixture of Ingredients)

A solution was prepared by mixing 882.8 g ammonium heptamolybdate tetrahydrate and 4605 g water. To this solution was added 175.5 g ammonium metavanadate and 121.7 g $Sb_2O_3$. The mixture was heated to 90° C. and stirred for 2.5 hours. The solution was then cooled to 70° C. and 1883 g of a Nalco silica sol (96SN036, 32% solids) and 176.6 g of 30% $H_2O_2$ was added. The solution was stirred for 1 hour at 50° C. (Mixture 1)

Another mixture was prepared by adding 24.1 g of $Sb_2O_3$ to a 626 g of a 0.6 molar (in Nb) niobic acid/oxalic acid solution, previously prepared. To this mixture were added 152.9 g of 30% $H_2O_2$, 6.8 g Ce(acetate)$_3$.1.5$H_2O$ and 40 g of $TiO_2$. The mixture was stirred for 30 min at room temperature (Mixture 2).

(Preparation of a Dried Catalyst Precursor)

Mixture 2 was added to Mixture 1 while stirring. To this was added a solution prepared by mixing 73.6 g fumed silica and 1125 g water. The final mixture was stirred for 15 min and spray dried.

(Calcination to Form a Mixed Oxide Catalyst)

About 75 g of this spray-dried material was calcined under nitrogen in a 1-foot vertical tube in two steps. After raising the temperature of the loaded vertical tube at the rate of about 1.2° C./min, to 345° C., the temperature was maintained at 345° C. for 4 hours. In the $2^{nd}$ step the temperature was again raised at the rate of about 2.3° C./min to a temperature of 630° C. This calcination was completed in 2 hours by maintaining the temperature at 630° C. This catalyst was evaluated in a 40 cc fluid bed reactor

TABLE

Catalyst Performance, M1 cell volume, and Aspect ratio

| Ex. | Run Temp °C. | Feed ratio C3:NH3:Air | WWH | P, psig | AN yield | C3 conv | AN select | M1 Cell vol. $A^3$ | Aspect Ratio |
|---|---|---|---|---|---|---|---|---|---|
| 1 | 430 | 1:1.35:16 | 0.1 | 8 | 20.8 | 76.7 | 27.2 | 2249 | 2.5 |
| 1 | 440 | 1:1.2:16 | 0.075 | 5.4 | 20.8 | 81.7 | 25.5 | 2249 | 2.5 |
| 2 | 430 | 1:1.0:13 | 0.1 | 3.0 | 27.2 | 75.4 | 36.1 | 2253 | 2.2 |
| 2 | 431 | 1:1.0:13 | 0.1 | 3.0 | 25.3 | 74.9 | 33.8 | 2253 | 2.2 |
| 3 | 430 | 1:135:16 | 0.056 | 9.0 | 32.8 | 76.1 | 43.0 | 2257 | 2.2 |
| 3 | 440 | 1:1.45:16 | 0.056 | 9.0 | 32.7 | 83.6 | 39.1 | 2257 | 2.2 |
| 4 | 430 | 1:1.35:16 | 00.56 | 4 | 38.5 | 72.4 | 53.2 | 2263 | 1.3 |
| 4 | 443 | 1:1.35:16 | 0.056 | 4 | 41.0 | 78.5 | 52.2 | 2263 | 1.3 |
| 4 | 444 | 1:1.35:16 | 0.056 | 10 | 37.6 | 83.9 | 44.8 | 2263 | 1.3 |
| 5 | 430 | 1:1.35:16 | 0.056 | 6 | 40.1 | 78.7 | 51.0 | 2261 | 1.2 |
| 5 | 440 | 1:1.4:16 | 0.056 | 5 | 41.5 | 84.1 | 49.3 | 2261 | 1.2 |
| 6 | 430 | 1:1.35:16 | 0.075 | 10 | 35.8 | 75.7 | 49.1 | 2259 | 2.1 |
| 6 | 440 | 1:1.2:16 | 0.056 | 9.5 | 33.5 | 88 | 38.1 | 2259 | 2.1 |
| 7 | 440 | 1:1.35:16 | 0.49 | 4.0 | 40.4 | 75 | 53.8 | 2266 | 1.4 |
| 7 | 440 | 1:1.35:16 | 0.49 | 4.0 | 37.5 | 73.5 | 51.0 | 2266 | 1.4 |

For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear, substantially is to be regarded as about twenty percent or more. The term "a feedstock consisting essentially of" is defined as at least 95 percent of the feedstock by volume. The term "essentially free of" is defined as absolutely except that small variations which have no more than a negligible effect on macroscopic qualities and final outcome are permitted, typically up to about one percent.

That which is claimed is:

1. A solid composition that exhibits catalytic activity for ammoxidation or oxidation of propane and iso-butane in the gaseous phase, which comprises one or more crystalline phases at least one of which is a first phase characterized as having the M1 crystalline structure, wherein said first phase has a unit cell volume in a range upward from 2250 $A^3$ to about 2350 $A^3$, a first crystallite dimension and a transverse thereto a second dimension with the proviso that the ratio of first to second dimensions is in a range downward from about 2.5 to about 0.7; and wherein at least a portion of the composition is formed under conditions of crystallization by combining sources of metal ions in amounts consistent with a nominal mixed oxide material represented by the empirical formula:

$$MoV_aSb_bNb_cO_\delta$$

Where $0.1 < a < 1.0$,
$0.01 < b < 1.0$,
$0.001 \le c \le 0.25$, and

δ is the number of oxygen atoms required to maintain electro-neutrality of the other component elements present.

2. The solid composition of claim 1 wherein at least a portion of the crystalline material is formed by a process which comprises combining the sources of metal ions in aqueous solutions, drying the resulting combined mixture to recover solid materials, and maintaining the recovered solids at elevated temperatures for times sufficient to form at least the first crystalline phase.

3. The composition of claim 1 wherein the first phase is characterized as having the M1 crystalline structure that has a unit cell volume in a range upward from 2255 $A^3$ to about 2290 $A^3$, a major dimension and transverse thereto a second dimension with the proviso that the ratio of major to transverse dimensions is in a range downward from about 1.75 to about 0.7.

4. The composition of claim 1 further comprising tellurium (Te).

5. A solid composition that exhibits catalytic activity for ammoxidation or oxidation of propane and iso-butane in the gaseous phase, which comprises one or more crystalline phases at least one of which is a first phase characterized as having the M1 crystalline structure, wherein said first phase has a unit cell volume in a range upward from 2250 $A^3$ to about 2350 $A^3$, a first crystallite dimension and a transverse thereto a second dimension with the proviso that the ratio of first to second dimensions is in a range downward from about 2.5 to about 0.7; and wherein at least a portion of the composition is formed under conditions of crystallization by combining sources of metal ions in amounts consistent with a nominal mixed oxide material represented by the empirical formula:

$$MoV_aSb_bNb_cX_dA_fO_\delta$$

Where
X is selected from the group consisting of Ti, Sn, Ge, Zr, Hf; and mixtures thereof,
A is selected from the group consisting of Ce, Nd and mixtures thereof,
0.1<a<1.0,
0.01<b<0.5,
0.001<c<0.25,
0.005<d<0.4,
0≤f<0.1, and
δ is the number of oxygen atoms required to maintain electro-neutrality of the other component elements present with the proviso that one or more of the other elements in the mixed oxide can be present in an oxidation state lower than its highest oxidation state.

6. The composition of claim 5 wherein the first phase is characterized as having the M1 crystalline structure that has a unit cell volume in a range upward from 2255 $A^3$ to about 2290 $A^3$, a first dimension and transverse thereto a second dimension with the proviso that the first of major to second dimensions is in a range downward from about 1.75 to about 1.0.

7. The solid composition of claim 5 wherein at least a portion of the crystalline material is formed by a process which comprises combining the sources of metal ions in aqueous solutions or aqueous mixtures, drying the resulting aqueous mixture to recover solid materials, and maintaining the recovered solids at elevated temperatures for times sufficient to form at least the first crystalline phase.

8. The composition of claim 5 wherein the aqueous mixtures are reacted at temperatures below about 100° C. and ambient, or near ambient, pressure, and the recovered solid materials are first maintained at elevated temperatures of no more than about 400° C., and thereafter in a range upward from about 550° C. to 700° C. and ambient, or near ambient, pressure.

9. The solid composition of claim 5 wherein at least a portion of the crystalline material is formed by a process which comprises combining the sources of metal ions in aqueous solutions or aqueous mixtures, maintaining the resulting aqueous mixture at elevated temperatures and pressures for times sufficient to form at least the first crystalline phase.

10. The composition of claim 5 wherein the composition that exhibits catalytic activity for ammoxidation of propane in the gaseous phase comprises a mixed metal oxide in particulate form comprising, as component elements, molybdenum (Mo), vanadium (V), antimony (Sb) titanium (Ti), and niobium (Nb).

11. The catalyst composition of claim 5 wherein the composition that exhibits catalytic activity for ammoxidation of propane in the gaseous phase comprises a mixed metal oxide in particulate form having, as component elements, molybdenum (Mo), vanadium (V), antimony (Sb) niobium (Nb), titanium (Ti), and cerium (Ce).

12. A solid composition that exhibits catalytic activity for ammoxidation or oxidation of propane and iso-butane in the gaseous phase, which comprises one or more crystalline phases at least one of which is a first phase characterized as having the M1 crystalline structure, wherein said first phase has a unit cell volume in a range upward from 2250 $A^3$ to about 2350 $A^3$, a first crystallite dimension and a transverse thereto a second dimension with the proviso that the ratio of first to second dimensions is in a range downward from about 2.5 to about 0.7; and wherein at least a portion of the composition is formed under conditions of crystallization by combining sources of metal ions in amounts consistent with a nominal mixed oxide material represented by the empirical formula:

$$MoV_aSb_bNb_cTi_dO_\delta$$

Where
0.1<a<1.0,
0.01<b<1.0,
0.01<c<0.25,
0.005<d<0.4, and
δ is the number of oxygen atoms required to maintain electro-neutrality of the other component elements present.

* * * * *